(12) United States Patent
Overtoom (10) Patent No.: US 10,449,327 B2
(45) Date of Patent: Oct. 22, 2019

(54) CATHETER SYSTEM FOR DELIVERY OF A URETERAL CATHETER

(71) Applicant: Overtoom Limited, Dublin (IE)

(72) Inventor: Timotheus Theodorus Cornelis Overtoom, Bilthoven (NL)

(73) Assignee: Overtoom Limited, Dublin (IE)

( * ) Notice: Subject to any disclaimer, the term of this patent is extended or adjusted under 35 U.S.C. 154(b) by 207 days.

(21) Appl. No.: 15/508,504

(22) PCT Filed: Sep. 18, 2015

(86) PCT No.: PCT/EP2015/071500
§ 371 (c)(1),
(2) Date: Mar. 3, 2017

(87) PCT Pub. No.: WO2016/042150
PCT Pub. Date: Mar. 24, 2016

(65) Prior Publication Data
US 2017/0274178 A1  Sep. 28, 2017

(30) Foreign Application Priority Data
Sep. 19, 2014 (NL) .................................. 2013498

(51) Int. Cl.
*A61M 25/00* (2006.01)
*A61M 27/00* (2006.01)
*A61M 25/01* (2006.01)

(52) U.S. Cl.
CPC ...... *A61M 25/0017* (2013.01); *A61M 27/008* (2013.01); *A61M 25/0102* (2013.01); *A61M 2025/0063* (2013.01)

(58) Field of Classification Search
CPC ............ A61M 25/0017; A61M 27/008; A61M 2025/0063; A61M 25/0102;
(Continued)

(56) References Cited

U.S. PATENT DOCUMENTS 4,990,133 A * 2/1991 Solazzo .............. A61M 27/008
604/544
5,213,575 A * 5/1993 Scotti .................... A61M 25/01
604/284
(Continued)

FOREIGN PATENT DOCUMENTS

DE    3816906 A1    11/1989
EP    0 365 269 A1    4/1990
(Continued)

*Primary Examiner* — Adam Marcetich
(74) *Attorney, Agent, or Firm* — Hoffmann & Baron, LLP (57) ABSTRACT

A catheter system for delivery of a ureteral catheter in a ureter includes a ureteral catheter, a pusher catheter to deliver the ureteral catheter at a desired location, and a connection device, to connect, in an assembled state a distal end of the pusher catheter to a proximal end of the ureteral catheter. The catheter further includes a releasable tether to secure a connection of the connection device between the ureteral catheter and the pusher catheter. The connection device includes a connector element provided on the ureteral catheter, and a sleeve provided on the pusher catheter, where the connector element is configured to be arranged in the sleeve, and that the tether is arranged to prevent unintentional release of the connector element out of the sleeve.

21 Claims, 4 Drawing Sheets

(58) Field of Classification Search
CPC .. A61M 25/0026; A61M 25/09; A61M 25/10; A61M 31/005; A61M 39/105; A61M 25/01; A61M 2025/0175; A61M 25/0194; A61M 2210/1082; A61F 2/04; A61F 2002/048
See application file for complete search history.

(56) References Cited

U.S. PATENT DOCUMENTS

| | | | | |
|---|---|---|---|---|
| 5,334,185 | A * | 8/1994 | Giesy | A61B 17/3415 604/170.01 |
| 6,066,113 | A | 5/2000 | Overtoom | |
| 6,652,569 | B1 | 11/2003 | Taylor et al. | |
| 2005/0085892 | A1* | 4/2005 | Goto | A61F 2/94 623/1.12 |
| 2006/0116714 | A1* | 6/2006 | Sepetka | A61B 17/12022 606/200 |
| 2007/0179588 | A1* | 8/2007 | Balgobin | A61B 17/0057 623/1.11 |
| 2007/0276466 | A1 | 11/2007 | Lavelle et al. | |
| 2007/0293929 | A1* | 12/2007 | Aoba | A61F 2/95 623/1.11 |
| 2009/0247990 | A1* | 10/2009 | Ovcharchyn | A61M 25/04 604/533 |
| 2010/0262219 | A1* | 10/2010 | Frimerman | A61F 2/013 623/1.11 |
| 2011/0077622 | A1 | 3/2011 | Weisman et al. | |
| 2012/0165827 | A1* | 6/2012 | Khairkhahan | A61N 1/362 606/129 |
| 2012/0303109 | A1* | 11/2012 | Okuma | A61F 2/95 623/1.11 |
| 2015/0051609 | A1* | 2/2015 | Schmidt | A61N 1/362 606/129 |
| 2015/0051611 | A1* | 2/2015 | Schmidt | A61N 1/37205 606/129 |
| 2015/0306381 | A1* | 10/2015 | Schmidt | A61N 1/0587 607/120 |

FOREIGN PATENT DOCUMENTS

| | | |
|---|---|---|
| EP | 2 818 141 B1 | 4/2017 |
| JP | H 2-168941 A | 6/1990 |
| JP | 5408682 B1 | 2/2014 |
| WO | 00/69498 A1 | 11/2000 |
| WO | 2008/155672 A2 | 12/2008 |
| WO | 2012/068508 A1 | 5/2012 |

* cited by examiner

CATHETER SYSTEM FOR DELIVERY OF A URETERAL CATHETER

CROSS-REFERENCE TO RELATED APPLICATIONS

This application is the National Stage of International Application No. PCT/EP2015/071500 filed Sep. 18, 2015, which claims the benefit of Netherlands Application No. NL 2013498, filed Sep. 19, 2014, the contents of which is incorporated by reference herein.

FIELD OF THE INVENTION

The present invention relates to a catheter system for delivery of a ureteral catheter in a ureter for treatment of the ureter and/or the pyelo-ureter junction. The invention also relates to the use of a catheter system for the treatment of a diseased, in particular stenosed ureter of a patient, and a method for delivery of a ureteral catheter in a patient's ureter.

BACKGROUND OF THE INVENTION

Blockages in the ureter which are generally caused by constriction thereof, such as a stenosis and/or the presence of kidney stones, can lead to serious medical problems such as pain, inflammation of the ureter wall and prevention of urine drainage from the kidney.

A ureteral catheter, sometimes also called ureteral or ureteric stent, is a thin tube inserted into the ureter to prevent or treat obstruction of the urine flow from the kidney and/or to ensure the patency of a ureter. The provision of a ureteral catheter may be a temporary provision, but a ureteral catheter may also placed in the ureter for longer periods. The length of the ureteral catheter used in adult patients may for example vary between 24 to 30 cm.

One or both ends of the ureteral catheter may be coiled to prevent it, after placement, from moving out of place. Such ureteral catheter is often referred to as a double J catheter or also JJ catheter or pig-tail catheter.

A ureteral catheter can be placed in the ureter cystoscopically or percutaneously. In the first method, the ureteral catheter is introduced into the ureter from the bladder towards the kidney of the patient. In a percutaneous placement method of the ureteral catheter, the ureteral catheter is inserted through an incision into the patient's body and brought into the kidney and subsequently through the ureter until a distal end of the catheter reaches a desired location in the bladder.

In both methods, accurate placement of the ureter catheter is important. In particular, the catheter ends in both the pyelum and bladder should be correctly placed to avoid tissue damage and/or discomfort to the patient.

The ureteral catheter may be connected with a proximal end to a distal end of a so-called pusher catheter with which the ureteral catheter can be moved towards and into the desired implantation position. When the ureteral catheter is correctly positioned, the ureteral catheter may be released from the pusher catheter, and the pusher catheter can be pulled back out of the body of the patient being treated.

For proper placement of the ureteral catheter an easy release of the ureteral catheter from the pusher catheter is desirable. At the same an unintentional and/or premature release of the ureteral catheter is undesirable, in particular when the ureteral catheter has not yet been positioned at the desired location in the ureter. Unintentional and/or premature release may for instance occur when the combination of pusher catheter and ureteral catheter is pulled back, i.e. in proximal direction. Generally, unintentional and/or premature release of the ureteral catheter should be prevented.

To avoid such premature release of the ureteral catheter from the pusher catheter, it is known to provide a tether, which is connected to the ureteral catheter. When the combination of pusher catheter and ureteral catheter is pulled back, i.e. in proximal direction, the tether may be pulled to reduce the risk of unintentional and/or premature release of the ureteral catheter.

SUMMARY OF THE INVENTION

It is an object of the invention to provide a catheter system for the delivery of a ureteral catheter in a ureter, which substantially reduces the risk of unintentional and/or premature release of the ureteral catheter, or at least to provide an alternative catheter system.

The invention provides a catheter system for delivery of a ureteral catheter in a ureter, comprising:
a ureteral catheter,
a pusher catheter to deliver the ureteral catheter at a desired location,
a connection device, to connect, in an assembled state a distal end of the pusher catheter to a proximal end of the ureteral catheter,
characterized in that the connection device comprises a connector element provided on the ureteral catheter, and a sleeve provided on the pusher catheter, wherein the connector element is configured to be arranged in the sleeve to releasably connect the ureteral catheter to the pusher catheter, and that the tether is arranged to prevent unintentional release of the connector element out of the sleeve.

The catheter system comprises an ureteral catheter to be placed in a patient's ureter, and a pusher catheter to advance the ureteral catheter by pushing towards the desired location in the ureter. The catheter system may further comprise a guide wire over which the pusher catheter and the ureteral catheter can be moved towards the desired location.

The pusher catheter and the ureteral catheter are connected to each other by a connection device. The connection device comprises a sleeve that can be arranged about the distal end of the pusher catheter and the proximal end of the ureteral catheter to hold these ends together.

The connection device may be an integral part of the pusher catheter and/or the ureteral catheter. For example, the sleeve may be fixed to a distal end of the ureteral catheter to receive a proximal end of the ureteral catheter therein.

In an embodiment, the connector element is made of a relatively hard material with respect to other parts of the ureteral catheter. Such relatively hard connector element is more suitable to be used in the connection device. The connector element which is preferably cylindrical in shape, is configured to be arranged with friction fit in the sleeve. The connector element may have a larger diameter than the diameter of the other parts of the ureteral catheter.

In an embodiment, a hollow needle/mini tube may be arranged between the pusher catheter and the ureteral catheter, i.e. the hollow needle/mini tube extends, with friction fit, in aligned openings or lumina of the pusher catheter and the ureteral catheter to further improve the connection force between the pusher catheter and the ureteral catheter.

The connection device to connect the pusher catheter to the ureteral catheter comprises at an end thereof a sleeve, for example a cover tube mounted to one of the ureteral catheter and the pusher catheter, while the other comprises a connector element to be placed in the sleeve. Such connection is in particular suitable to push the ureteral catheter in the distal direction, but when the ureteral catheter is pulled back in the proximal direction, this connection may not provide sufficient coupling strength to avoid unintentional release of the ureteral catheter.

To secure the connection device a releasable tether is provided.

In an embodiment, the tether runs, in an assembled state of the catheter system, through one or more lumina of the pusher catheter. The one or more lumina of the pusher catheter are one or more channels, preferably internal channels, running over at least a part of the length of pusher catheter. By making the tether run through the pusher catheter, the tether no longer runs freely through the body of the patient next to the pusher catheter. This substantially reduces the risk of the tether becoming clamped or stuck in the body of the patient, for instance between the catheter system and a part of the body of the patient.

The one or more lumina of the pusher catheter through which the tether is guided may be formed by separate tether lumina in the pusher catheter and/or by lumina also having another function such as a guide wire lumen for guiding a guide wire or a contrast agent lumen for transporting a contrast agent.

In an embodiment, the tether runs at least in the pusher catheter internally back and forth from a distal end to a proximal end of the pusher catheter through one or more lumina of the pusher catheter. By making the tether run internally back and forth from a distal end to a proximal end of the pusher catheter through one or more lumina of the pusher catheter, the tether runs substantially completely within the pusher catheter between its proximal end and its distal end. Therewith the risk of becoming clamped or stuck in the body of the patient, for instance between the catheter system and a part of the body of the patient is further reduced In an embodiment, the ureteral catheter comprises an arrangement to receive a loop of the tether. The arrangement that receives the loop assures that when two tether ends at opposite sides of the loop are tightly held or pulled, the loop will be held by the arrangement so that the ureteral catheter cannot substantially move away from the pusher catheter.

Any other arrangement to releasably secure the tether to the ureteral catheter to prevent unintentional release of the ureteral catheter from the pusher catheter may also be applied.

In an embodiment, the arrangement comprises a tether opening between two inner lumina in the ureteral catheter, wherein the loop of the tether is guided through the tether opening from one of the two inner lumina to another of the two inner lumina.

By providing a tether opening in the ureteral catheter through which the tether can be guided from one lumen of the ureteral catheter to another lumen of the ureteral catheter, a securing position for a loop of the tether can be created. By holding both tether ends at opposite sides of the loop, the connection between the pusher catheter and the ureteral catheter can be secured. By pulling at one of the tether ends, while releasing the other tether end, the tether can be pulled out of the catheter system, therewith making release of the ureteral catheter from the pusher catheter possible.

In an alternative embodiment, the arrangement comprises two tether openings between an outer surface of the ureteral catheter and one or more inner lumina in the ureteral catheter, wherein the loop of the tether is guided through each of the two tether openings, such that a part of the loop of the tether runs over the outer surface of the ureteral catheter. In such embodiment in which the loop is guided over the outer surface of the pusher catheter, the loop can hold the ureteral catheter in aligned position with the pusher catheter.

In another embodiment, the connection device comprises a sleeve mounted on the distal end of the pusher catheter and a connector element at the proximal end of the ureteral catheter, which connector element, in assembled state of the catheter system, is arranged in the sleeve. In such embodiment, the arrangement to receive a loop may comprise two first tether openings between an outer surface of the connector element of the ureteral catheter and one or more inner lumina in the ureteral catheter, and two second tether openings in the sleeve such that the loop of the tether may be guided through each of the two first tether openings and the two second tether openings, such that a part of the loop of the tether runs over the outer surface of the sleeve. In such embodiment in which the loop is guided over the sleeve of the pusher catheter, the loop can also hold the ureteral catheter in aligned position with the pusher catheter.

Other embodiments in which the loop runs over the outer surface of the ureteral catheter and/or pusher catheter may also be contemplated.

In an embodiment, the outer surface of the ureteral catheter comprises a groove to at least partially receive the securing loop of the tether. By creating a groove in the outer surface of the ureteral catheter, the tether can relatively easy be arranged in the groove and the presence of the tether can be checked. Furthermore, the outer diameter of the catheter system may not be increased or increased substantially less due to the presence of the loop of the tether.

In an embodiment in which the tether is guided over the outer surface of the sleeve in which the connector element is arranged, the tether may partially be pulled into groove due to flexibility of the sleeve.

In an embodiment, the groove comprises a guiding surface that gradually guides the tether from a substantially longitudinal direction to a substantially tangential direction. By providing these guiding surface, the pulling force required to pull a tether out of the connector element may be reduced.

In embodiments, guiding surfaces may be provided to guide the tether gradually from a first orientation to a second orientation.

In an embodiment, the one or more inner lumina are only used to receive the tether. For example, the pusher catheter may comprise one or two separate tether lumina in the pusher catheter to receive the tether. In alternative embodiments, one or more inner lumina of the pusher catheter to receive the tether are formed by lumina also having another function such as a guide wire lumen, a contrast agent lumen, a fluid connection lumen or any other lumen. The fluid connection lumen may for example be used to inflate and/or deflate a balloon arranged at a distal end of the ureteral catheter.

In an embodiment, a first tether end is locked at a first locking location and a second tether end opposed to the first tether end is locked at a second locking location, wherein a tether length between the first locking location and the second locking location is selected to prevent release of the ureteral catheter from the pusher catheter before release of the first or second tether end from the at the first or second locking location, respectively. The first and/or second locking location is preferably arranged near a proximal end of the pusher catheter such that the first and/or second locking location can be operated by the user in order to release the tether from the first and/or second locking location, respectively.

By locking a first tether end and a second tether end in this way, the ureteral catheter cannot be released from the pusher catheter before at least one of the first and second tether ends is released from the locking state. This further ensures that the ureteral catheter is not unintentionally and/or prematurely released from the pusher catheter before the tether is released from one of the first locking location and the second locking location.

In an embodiment, the first locking location is a first clamping location where the first tether end is clamped and/or the second locking location is a second clamping location where the second tether end is clamped. Clamping of the tether can effectively be used to lock the tether at the first and/or second locking location. Clamping can be realized by two parts that are held together such that the tether is held and locked between the two parts.

In an embodiment, the first clamping location is formed by a first screw connection of the catheter system and the second clamping location is formed by a second screw connection. Screw connections can be used to clamp the tether. The screw connection may be any screw connection of the catheter system, for example a connection between a Y connector and the pusher catheter, or screw connections between other parts of the catheter system.

In an embodiment, the catheter system comprises a tether locking device comprising a first screw element having an inner screw thread that mates with an outer screw thread on the proximal end of the pusher catheter to provide the first screw connection, and a second screw element which comprises an inner screw thread that mates with an outer screw thread on a proximal end of the first screw element to provide the second screw connection.

In an embodiment one of the first tether end and the second tether end is, during assembly, permanently locked at the respective first or second locking location, and wherein, during assembly, the other of the first tether end and the second tether end is releasably locked at the respective first or second locking location.

Permanent locking means that the locking in the respective clamping location cannot be released without damage to one or more parts of the catheter system. For example, the locking may be realized by glue, for example by gluing two parts of a screw connection after the tether has been clamped between the two parts by screwing the two part together.

In an embodiment, the connection device to connect the pusher catheter to the ureteral catheter comprises at an end thereof a sleeve, for example a cover tube mounted to one of the ureteral catheter and the pusher catheter, while the other comprises a connector element to be placed in the sleeve.

In an embodiment, the connection device comprises a hollow needle arranged, in the assembled state, in a proximal end of the auxiliary lumen and a distal end of the second auxiliary lumen. Such needle can provide a connection to hold the pusher catheter as long as the ureteral catheter is not to be released from the pusher catheter.

In an embodiment, the ureteral catheter comprises a guide wire lumen and the pusher catheter comprises a second guide wire lumen, wherein a diameter of the second guide wire lumen is larger than a diameter of at least the proximal end of the guide wire lumen, such that the ureteral catheter can be released from the pusher catheter by advancing a pusher element through the second guide wire lumen and pushing therewith against the proximal end of the ureteral catheter.

The difference in diameter between the diameter of the second guide wire lumen and the diameter of at least the proximal end of the guide wire lumen provides a surface against which a pusher element can be pushed. When sufficient force is exerted on this surface the connector element will be pushed out of the sleeve and therewith the ureteral catheter will be released from the pusher catheter. In an embodiment, the ureteral catheter is a double J catheter, such as for example disclosed in US application number US 2007/0276466 or a ureteral balloon catheter, as for example disclosed in U.S. Pat. No. 6,066,113.

The invention further relates to the use of a catheter system for the treatment of a diseased, in particular stenosed ureter of a patient, and to a method for delivery of a ureteral catheter in a patient's ureter, wherein the use or method comprises the steps of:

inserting, in assembled state, the catheter system into the patient to place the ureteral catheter in the ureter to be treated;

releasing and pulling out of the tether from the catheter system;

releasing at a desired location the ureteral catheter from the pusher catheter; and retracting the pusher catheter from of the patient.

BRIEF DESCRIPTION OF THE DRAWINGS

Further characteristics and advantages of the invention will now be elucidated by a description of an embodiment of the invention, with reference to the accompanying drawings, in which.

DETAILED DESCRIPTION OF THE INVENTION

Figures 1, 2A:
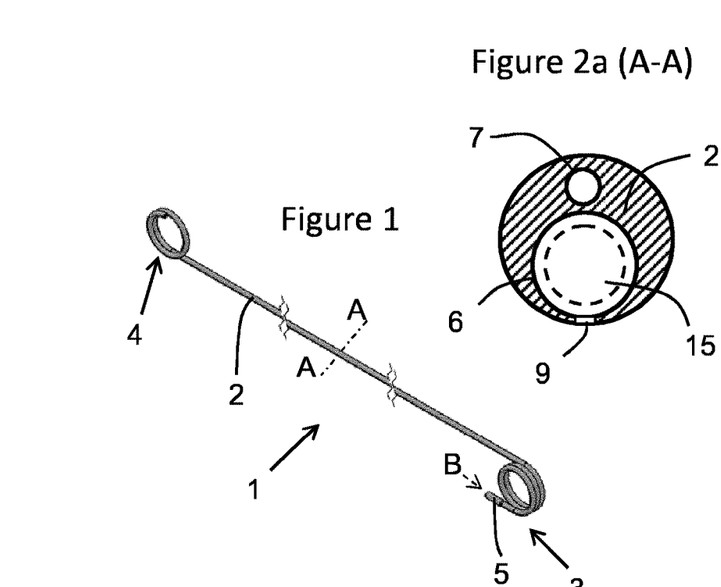
FIG. 1 shows a perspective view of a ureteral catheter according to an embodiment of the invention.
FIG. 2*a* shows a cross section A-A of the ureteral catheter of FIG. 1.

FIG. 1 shows a perspective view of a ureteral catheter, in particular a double J catheter, generally indicated by reference numeral 1. The ureteral catheter 1 comprises an elongate body 2 having a proximal end 3 and a distal end 4. The proximal end 3 comprises a widened connector element 5, also referred to as overmould, configured to connect the ureteral catheter 1 to a pusher catheter. This connector element 5 may be made of relative hard material compared to the further parts of the ureteral catheter to make a more reliable connection to the pusher catheter possible.

The ureteral catheter 1 is configured to be placed in the ureter to be treated typically to restore and/or ensure patency of the ureter. After positioning of the ureteral catheter 1 in the ureter, the ureteral catheter 1 will extend from the bladder to the pyelum.

The proximal end 3 and the distal end 4 are formed as a pigtail or coil to make sure that the respective ends remains properly positioned in the bladder and/or pyelum, respectively, in which it is placed. The proximal end 3 and the distal end 4 of the ureteral catheter are suitable to be placed in both the pyelum and the bladder, dependent on the direction of introduction into the ureter.

FIG. 2a shows a cross-section A-A of the ureteral catheter 1 in the elongate middle part thereof. The ureteral catheter 1 comprises a guide wire lumen 6 and an auxiliary lumen 7. This auxiliary lumen 7 may for example be used for guiding a fluid contrast agent through the ureteral catheter 1 from the proximal end 3 to the distal end 4.

Both the guide wire lumen 6 and the auxiliary lumen 7 run from the proximal end 3 of the ureteral catheter 1 to the distal end 4 of the ureteral catheter 1. Over the relative straight middle part of the ureteral catheter 1, the auxiliary lumen 7 is preferably a closed channel to the outer surface of the ureteral catheter 1 such that from a proximal opening at the proximal end of the ureteral catheter 1, contrast agent or other fluids can be transported to a distal opening at the distal end of the ureteral catheter 1. In case such auxiliary lumen 7 is not needed, this auxiliary lumen may also be omitted.

The guide wire lumen 6 may have a number of drainage openings 9 along the length of the guide wire lumen to promote fluid flow through the ureter after placement of the ureteral catheter 1. These drainage openings 9 may improve the drainage effect of the ureteral catheter 1.

At the proximal end 3 and the distal end 4, the guide wire lumen 6 and the auxiliary lumen 7 comprise one or more openings to the outer side of the ureteral catheter 1. The distal end 4 of the ureteral catheter 1 may be tapered, preferably towards a diameter slightly larger than the guide wire lumen 6. The distal end of the auxiliary lumen 7 may be formed by an elongate opening or a side opening, for example in the tapered distal end of the ureteral catheter. The elongate opening or the side opening part is preferably designed to avoid or minimize scraping thereof against an inner wall of the ureter or other part of the patient's body.

The guide wire lumen 6 is configured to receive a guide wire 15, indicated by dashed lines in FIG. 2. The guide wire 15 can be used to guide the ureteral catheter 1 to the desired location in the ureter.

The diameter of the guide wire lumen 6 is substantially larger than the diameter of the guide wire 15 to obtain a space between the inner surface of the guide wire lumen 6 and the outer surface of the guide wire 15. This space can be used for the transport of fluid through the ureteral catheter when the guide wire 15 is still arranged in the guide wire lumen 6, but also facilitates sliding of the ureteral catheter 1 over the guide wire 15.

Figure 2B:
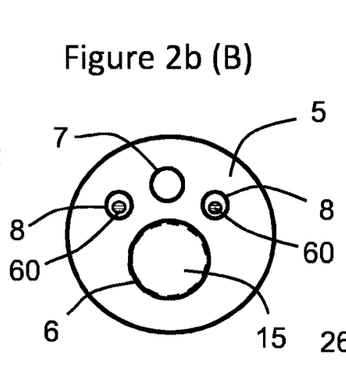
FIG. 2*b* shows a view B on the proximal end of the ureteral catheter of FIG. 1.

FIG. 2b shows a view B on the proximal end of the ureteral catheter 1. Also in this cross-section the guide wire lumen 6 and the auxiliary lumen 7 running over the length of the ureteral catheter 1 are shown. In addition, this part of the ureteral catheter 1 comprises two tether lumina 8 through each of which a tether 60 runs. The tether lumina 8 extend at the proximal end 3 only over a limited part of the length of the ureteral catheter 1, for example a few millimeters, for example the length of the connector element 5. As will be explained hereinafter this tether 60 is provided to prevent an unintentional release of the ureteral catheter 1.

In the connector element 5, the diameter of the guide wire lumen 6 is substantially the same as or slightly larger than the diameter of the guide wire 15 to obtain a relative tight fit between guide wire lumen 6 and guide wire, however without obstructing movement of the guide wire 15 with respect to the ureteral catheter 1. This tight fit is useful to make release of the ureteral catheter 1 from the pusher catheter 20 possible.

Figure 3:
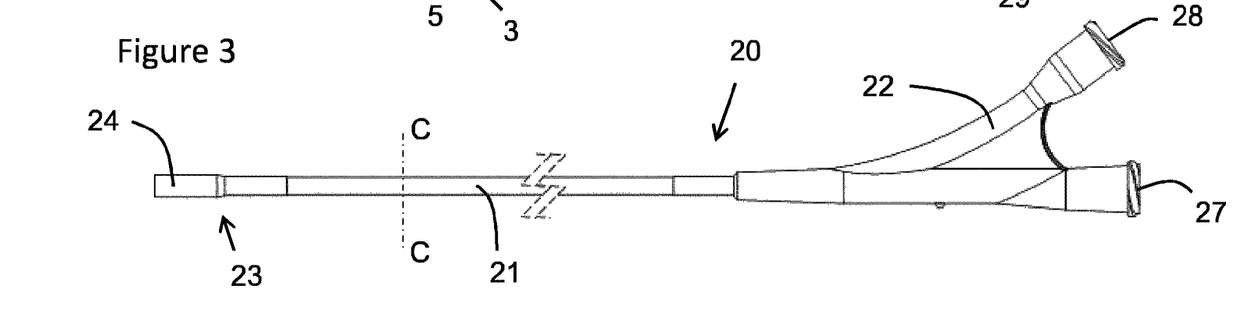
FIG. 3 shows a side view of a pusher catheter according to an embodiment of the invention.

FIG. 3 shows an embodiment of a pusher catheter 20. The pusher catheter 20 comprises an elongate pusher catheter body 21 and a Y shaped part 22. The pusher catheter 20 has a distal end. At the distal end 23 a distally extending sleeve 24, also referred to as cover tube, is provided to receive the connector element 5 of the ureteral catheter 1. By arranging the connector element 5 in the sleeve 24, the proximal end 3 of the ureteral catheter 1 may be connected to the distal end 23 of the pusher catheter 20. Additionally, or as an alternative, other connection means may be provided to couple the ureteral catheter 1 and the pusher catheter 20.

Figure 4:
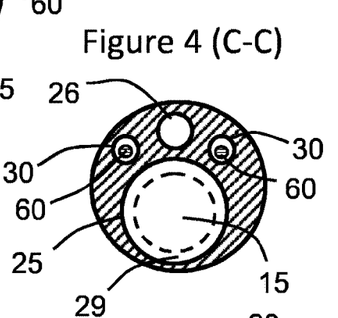
FIG. 4 shows a cross section C-C of the pusher catheter of FIG. 3.

FIG. 4 shows a cross section C-C of the pusher catheter 20. The pusher catheter 20 comprises a second guide wire lumen 25 and a second auxiliary lumen 26. Both the second guide wire lumen 25 and the second auxiliary lumen 26 run from a proximal end of the pusher catheter 20 to the distal end 23 of the pusher catheter 20. At the proximal end of the pusher catheter 20, the second guide wire lumen 25 is fluidly connected to a main port 27 of the pusher catheter 20 and the second auxiliary lumen 26 is connected to a side port 28 of the pusher catheter 20.

In the guide wire lumen 25 a guide wire 15 is shown, having the same diameter as the guide wire 15 in FIG. 2. The diameter of the second guide wire lumen 25 is larger than the diameter of the guide wire lumen 6. The space 29 in the second guide wire lumen 25 not occupied by the guide wire 15 may for example be used to transport contrast fluid from the main port 27 to the distal end 23 of the pusher catheter 20, but also facilitates movements of the guide wire 15 through the second guide wire lumen 25.

The pusher catheter 20 further comprises second tether lumina 30 configured to receive a tether 60. The second tether lumina 30 run over the entire length of the pusher catheter 20. At the distal end of the pusher catheter 20, the second tether lumina 30 are aligned with the tether lumina 8 such that the tether 60 may run from the second tether lumina 30 into the tether lumina 8 of the ureteral catheter 1.

It is remarked that in the shown embodiment of FIGS. 3 and 4, the pusher catheter 20 only comprises one guide wire lumen 25 and one auxiliary lumen 26. The term 'second' is used to distinguish the guide wire lumen 25 and the auxiliary lumen 26 of the pusher catheter 20 from the guide wire lumen 6 and the auxiliary lumen 7 of the ureteral catheter 1. Correspondingly, tether lumina refers to the lumina of the ureteral catheter configured to receive a tether 60, while second tether lumina refers to the lumina of the pusher catheter 20 configured to receive the tether 60.

Figure 5:
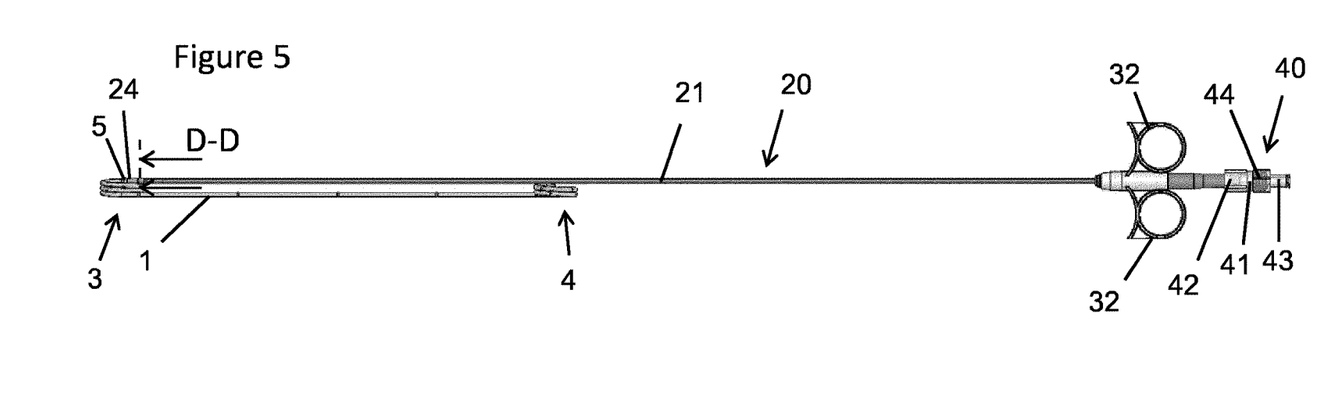
FIG. 5 shows a top view of an embodiment of a catheter system according to the invention.
Figure 6:
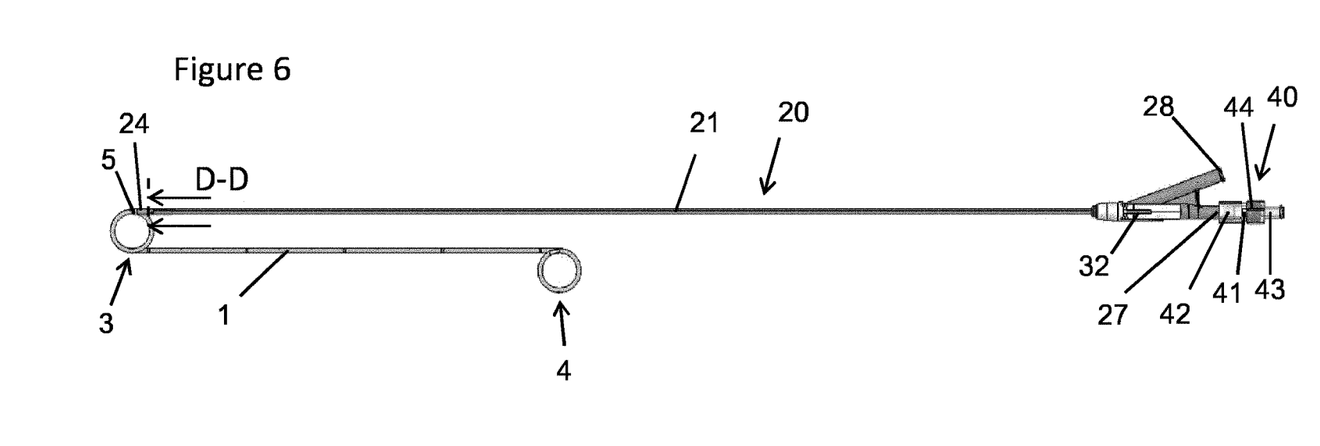
FIG. 6 shows a side view of the embodiment of FIG. 5.

FIGS. 5 and 6 show a catheter system for delivery of a ureteral catheter in a ureter. The catheter system comprises the ureteral catheter 1, as shown in FIG. 1, and a pusher catheter 20, as shown in FIG. 3, whereby the pusher catheter 20 is provided with finger grip devices 32 near its proximal end which enable the user to hold the pusher catheter, for example when pushing a pusher element through the pusher catheter to release the ureteral catheter 1 from the pusher catheter 20. On the main port 27 of the pusher catheter 20 a tether locking device 40 is mounted. The tether locking device 40 comprises a hollow channel which provides access to both the main port 27 of the second guide wire lumen 25 and proximal openings of the two second tether lumina 30.

The tether locking device 40 comprises a first screw element 41 having a first screw collar 42 with an inner screw thread that mates with an outer screw thread on the proximal end of the pusher catheter 20, such that the tether locking device 40 can be mounted on the proximal end of the pusher catheter 20.

The tether locking device 40 further comprises a second screw element 43 having a second screw collar 44 with an inner screw thread that mates with an outer screw thread on a proximal end of the first screw element 41.

Each of a first screw connection between the first screw collar 42 and the proximal end of the pusher catheter 20 and a second screw connection between the second screw collar 44 and the first screw element 41 may be used to clamp a tether 60.

In the assembled state of the catheter system, as shown in FIGS. 5 and 6, the guide wire lumen 6, the second guide wire lumen 25 and the hollow channel of the tether locking device 40 are aligned so that a guide wire 15 may run from the proximal end of the catheter system at a proximal end of the tether locking device 40 to the distal end of the catheter system to leave the ureteral catheter 1 at a guide wire opening at the distal end 4 of the ureteral catheter 1. The presence of a guide wire 15 in the guide wire lumen 6 of the ureteral catheter 1 may straighten the coiled ends of the ureteral catheter 1 (not shown) which facilitates movement of the catheter during placement in a patient. When the guide wire 15 is removed from the guide wire lumen 6 the proximal end 3 and the distal end 4 will return to the coiled shape, as shown in FIGS. 5 and 6.

The catheter system shown in FIGS. 5 and 6 comprises a tether 60 to secure the connection between the ureteral catheter 1 and the pusher catheter 20. This may be desirable to avoid an inadvertently release of the ureteral catheter 1 from the pusher catheter 20, for instance resulting from pulling back the pusher catheter 20 during positioning of the ureteral catheter 1.

The tether 60 comprises two tether ends connected by a loop 61. The loop 61 is formed around the outer surface of the ureteral catheter 1, near the proximal end 3 of the ureteral catheter 1.

Figure 7:
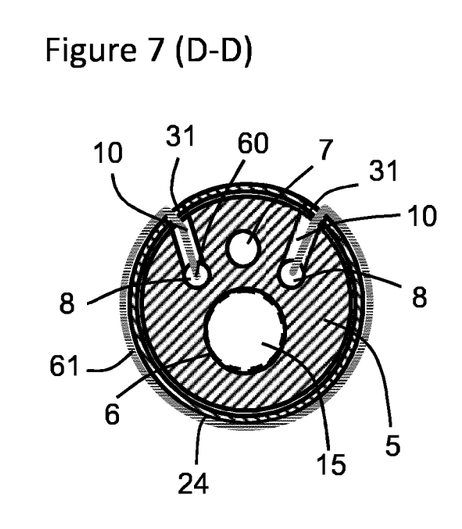
FIG. 7 shows a cross section D-D of a connection between the pusher catheter and the ureteral catheter of the embodiment of FIG. 5.

FIG. 7 shows a cross section of the catheter system at the location of the loop 61. This loop 61 is arranged at the location of the connection between the ureteral catheter 1 and the pusher catheter 20. At this location, the connector element 5 of the ureteral catheter 1 is arranged in a sleeve 24 of the pusher catheter 20. Two tether side openings 10 are provided between each of the tether lumina 8 and the outer surface of the pusher catheter 20.

Furthermore, the sleeve 24 comprises two tether openings 31 which are aligned with the tether side openings 10. The loop 61 runs from one of the tether lumina 8 through the tether side opening 10 and the tether opening 31 to the outer surface of the sleeve 24. The loop 61 then follows the outer surface of the sleeve 24 over a substantial part of the circumference of the sleeve 24, for example more than 270 degrees to the other tether opening 31 through which it runs to the other tether lumina 8 via the respective tether side opening 10.

The tether ends in both tether lumina 8 run via the tether lumina 8 and the second tether lumina 30 (see FIG. 4) to a proximal end of the pusher catheter 20. When the tether ends are held tight at the proximal end of the pusher catheter 20, the loop 61 ensures that the ureteral catheter 1 is not unintentionally released from the pusher catheter 20, since the loop 61 prevents movement of the connector element 5 out of the sleeve 24.

Figure 9:
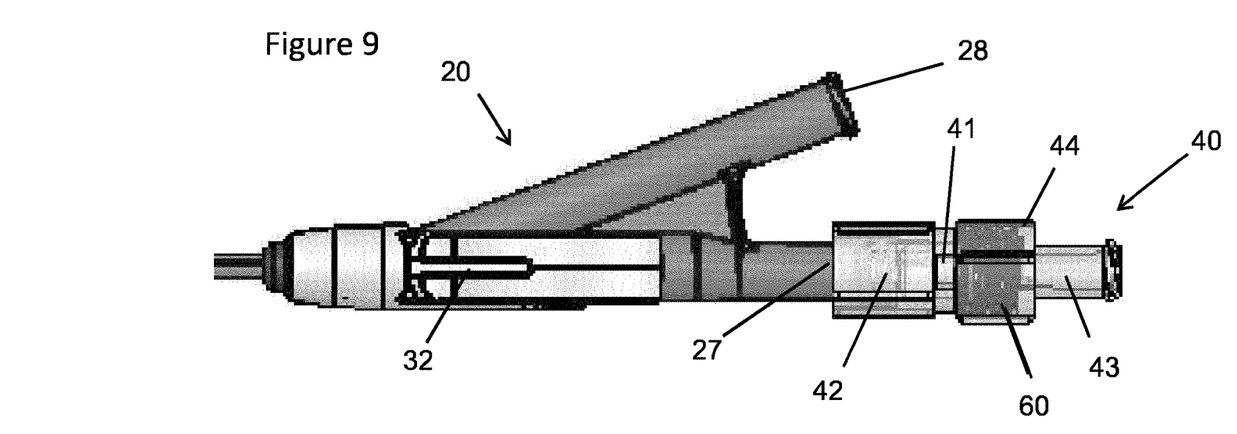
FIG. 9 shows the tether locking device of the embodiment of FIG. 5 in more detail.

In the embodiment as shown in FIGS. 5 and 6, a tether locking device 40 is provided, which tether locking device 40 is configured to hold the tether ends. FIG. 9 shows the tether locking device 40 mounted on the proximal end of the pusher catheter in more detail.

A first tether end is clamped in the first screw connection between the pusher catheter 20 and the first screw collar 42, the other second tether end is clamped in the second screw connection between the first screw element 41 and the second screw collar 44. The length of the tether between the part clamped by the first screw connection and the part clamped by the second screw connection, is selected such that tether prevents the connector element 5 to be pulled out of the sleeve 24.

At least one of the first screw connection and the second screw connection is releasable to release the tether in order to allow the pusher catheter and the ureteral catheter to be disconnected. This can be done by unscrewing the respective first or second screw connection. The other screw connection may be releasable, but may also be permanently locked, for instance by gluing the two parts of the screw connection together once the tether end is clamped in the screw connection.

In the embodiment of FIGS. 5 and 6, the first screw connection is releasable, but the second screw connection is permanently locked by gluing the first element 41 and the second screw collar 44 to each other. This second screw connection can only be released by damaging the parts of this screw connection. The advantage of permanently locking the screw connection is that the chance on unintentional release of the tether is further reduced.

In alternative embodiments, the tether 60 may not be locked in the catheter system. The user may lock the tether ends, for example by tying a knot or securing in another way at a suitable location. The tether ends may also be provided as loose ends which are slightly pulled by the surgeon when release of the ureteral catheter 1 may be expected, for example during pulling back of the complete catheter system.

The catheter system according to the invention makes accurate and secure placement of a ureteral catheter possible, both in a percutaneous delivery method and in a cystoscopical delivery of method. The procedure of accurate placement of the ureter may comprise the steps of inserting, in assembled state, the combination of ureter catheter and pusher catheter into the patient to place the ureter catheter in the ureter to be treated. The combination is preferably guided over a guide wire which already has been brought into the ureter.

When the ureteral catheter is positioned in the desired position in the ureter, the tether 60 may be unlocked at at least one of the locking locations, in particular by unscrewing one of the first and second screw connections. Thereafter, the tether 60 may at least partially be pulled out of the catheter system.

When the tether 60 is released at at least one side of the catheter system 60, and preferably removed from the catheter system by pulling it out, the ureteral catheter 1 may be released, for example by advancing a pusher element through the guide wire lumen of the pusher catheter to push and release the ureteral catheter from the pusher catheter. The pusher element may for example be used to push in the second guide wire lumen 25 against the proximal end of the ureteral catheter 1, as the cross section of the guide wire lumen 6 of the ureteral catheter 1 at this proximal end 3 is smaller than the cross section of the second guide wire lumen 25.

After release of the ureteral catheter from the pusher catheter, the pusher catheter may be retracted from the patient.

Figure 8:
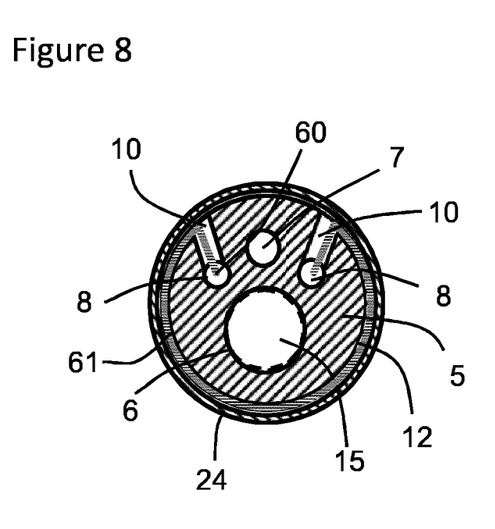
FIG. 8 shows a cross section of an alternative embodiment of the connection between the pusher catheter and the ureteral catheter.

FIG. 8 shows an alternative embodiment of the arrangement of the loop 61 in order to hold the connector element 5 in the sleeve 24 to avoid unintentional release of the ureteral catheter 1 from the pusher catheter 20. In the embodiment of FIG. 8, the outer surface of the connector element 5 comprises a circumferential groove 12 extending from one of the tether side openings 10 to the other of the tether side openings 10. The groove 12 has a depth substantially corresponding to a diameter of the tether 60. The sleeve 24 encloses the connector element 5 and the tether 60, in particular its loop 61, such that there is a friction fit between the connector element 5 and the tether 60.

In this embodiment, the sleeve 24 does not comprise any openings in its outer surface, and the tether loop does not run over the outer surface of sleeve 24. The advantage of such embodiment is that the outer surface of the catheter system that moves in the body of a patient is relatively smooth. However, the connection of the tether between the pusher catheter 20 and the ureteral catheter may be easier to release, in particular when the tether material can be stretched.

It is remarked that to smoothen the outer surface of the catheter system as shown in FIG. 7, also a groove 12 may be provided into which the tether loop 61 together with the sleeve 24 may be pulled to reduce the extent in which the tether loop 61 extends from the outer surface of the sleeve 24.

Figure 10:
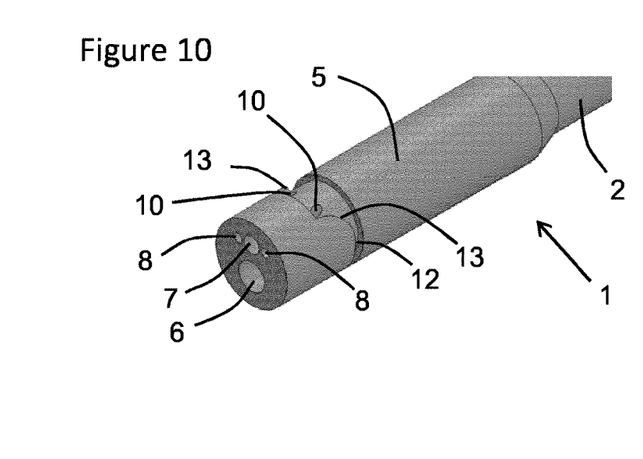
FIG. 10 shows an alternative embodiment of a connector element.

FIG. 10 shows a proximal end of an alternative embodiment of a pusher catheter 1. The pusher catheter 1 comprises a connector element 5 arranged at the proximal end of the elongate body 2. The connector element 5 comprises two tether lumina 8 configured to receive a tether 60. Each of the tether lumina 8 is connected via the tether side openings 10 with the groove 12. The groove 12 comprises next to the location of each of the tether side openings 10, a guiding surface 13 configured to guide the tether gradually from a substantially longitudinal direction to a substantially tangential direction. The advantage of these guiding surfaces 13 is that the pulling force required to pull the tether 60 out of the connector element 5 is reduced. In other embodiments, guiding surfaces to guide the tether gradually from a first orientation to a second orientation may be provided.

It is remarked that in the embodiments of catheter systems described hereinabove, all comprise separate tether lumina to receive a tether. However, in alternative embodiments the tether may also run through lumina having another function, such as a guide wire lumen or a fluid contrast agent lumen. Also, a single lumen may be used to guide two tether ends from the connection between the ureteral catheter and the pusher catheter to a proximal end of the pusher catheter. In some embodiments the tether may run outside the pusher catheter.

The different parts of the catheter system may be produced by any suitable method and from any suitable material known in the art. The ureteral catheter and the pusher catheter are preferably made from biocompatible plastics materials. The guide wire is preferably made of a biocompatible metal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A catheter system for delivery of a ureteral catheter in a ureter, comprising:
   a ureteral catheter,
   a pusher catheter to deliver the ureteral catheter at a desired location,
   a connection device configured to connect, in an assembled state, a distal end of the pusher catheter to a proximal end of the ureteral catheter,
   wherein the catheter system comprises a releasable tether configured to pass through a portion of the pusher catheter and to secure a connection of the connection device between the ureteral catheter and the pusher catheter,
   wherein the connection device comprises a connector element arranged at a proximal end of the ureteral catheter and a sleeve arranged at a distal end of the pusher catheter to releasably connect the ureteral catheter to the pusher catheter,
   wherein the connector element is configured to be arranged in the sleeve, and
   wherein the tether is arranged to prevent unintentional release of the connector element out of the sleeve.

2. The catheter system of claim 1, wherein the connector element is made of a relatively harder material than other parts of the ureteral catheter.

3. The catheter system of claim 2, wherein at least one of the one or more inner lumina of the pusher catheter to receive the tether is formed by a guide wire lumen of the pusher catheter and/or by a separate tether lumen in the pusher catheter.

4. The catheter system of claim 1, wherein the ureteral catheter comprises an arrangement to receive a loop of the tether.

5. The catheter system of claim 4, wherein the arrangement comprises a tether opening between two inner lumina of the ureteral catheter, wherein the loop of the tether is guided through the tether opening from one of the two inner lumina to another of the two inner lumina.

6. The catheter system of claim 5, wherein the one or more inner lumina are only used to receive the tether.

7. The catheter system of claim 4, wherein the arrangement comprises two tether openings between an outer surface of the ureteral catheter and one or more inner lumina of the ureteral catheter, wherein the loop of the tether is guided through each of the two tether openings, such that a part of the loop of the tether runs over the outer surface of the ureteral catheter.

8. The catheter system of claim 7, wherein the outer surface of the ureteral catheter comprises a circumferential groove to at least partially receive the securing loop of the tether.

9. The catheter system of claim 8, wherein the connector element comprises the circumferential groove.

10. The catheter system of claim 7, wherein the groove comprises a guiding surface that gradually guides the tether from a substantially longitudinal direction to a substantially tangential direction.

11. The catheter system of claim 7, wherein the part of the loop of the tether runs over the outer surface of the ureteral catheter at least partly in tangential direction with respect to the longitudinal axis of the ureteral catheter.

12. The catheter system of claim 4, wherein the connector element of the ureteral catheter comprises the arrangement to receive a loop of the tether.

13. The catheter system of claim 1, wherein the pusher catheter comprises two separate tether lumina to receive the tether in the pusher catheter.

14. The catheter system of claim 13, wherein, during assembly, one of the first tether end and the second tether end is permanently locked at the respective first or second locking location, and wherein, during assembly, the other of the first tether end and the second tether end is releasably locked at the respective first or second locking location.

15. The catheter system of claim 1, wherein a first tether end is locked at a first locking location and/or a second tether end opposed to the first tether end is locked at a second locking location, wherein a tether length between the first locking location and the second locking location is selected to prevent release of the ureteral catheter from the pusher catheter before release of the first or second tether end at the first or second locking location, respectively.

16. The catheter system of claim 15, wherein the first locking location is a first clamping location where the first tether end is clamped and/or wherein the second locking location is a second clamping location where the second tether end is clamped.

17. The catheter system of claim 16, wherein the first clamping location is formed by a first screw connection of the catheter system and/or the second clamping location is formed by a second screw connection of the catheter system.

18. The catheter system of claim 1, wherein the tether runs, in an assembled state of the catheter system, through one or more lumina of the pusher catheter, internally back and forth from a distal end to a proximal end of the pusher catheter through the one or more lumina of the pusher catheter.

19. The catheter system of claim 18, wherein the tether runs, in the assembled state of the catheter system, at least in the pusher catheter, internally back and forth from the distal end to the proximal end of the pusher catheter through the one or more lumina of the pusher catheter.

20. The catheter system of claim 1, wherein the ureteral catheter comprises a first guide wire lumen and the pusher catheter comprises a second guide wire lumen, and wherein a diameter of the second guide wire lumen is larger than a diameter of at least the proximal end of the first guide wire lumen, such that the ureteral catheter can be released from the pusher catheter by advancing a pusher element through the second guide wire lumen and pushing with the pusher element against the proximal end of the ureteral catheter.

21. Use of a catheter system for the treatment of a diseased ureter of a patient, inserting, in the assembled state, the catheter system as claimed in claim 1 into the patient to place the ureter catheter in the ureter to be treated;

releasing and pulling out the tether from the catheter system;

releasing at a desired location the ureteral catheter from the pusher catheter; and retracting the pusher catheter from of the patient.

* * * * *